United States Patent [19]

Wilk et al.

[11] Patent Number: 5,281,234
[45] Date of Patent: Jan. 25, 1994

[54] LAPAROSCOPIC SURGICAL METHOD AND RELATED INSTRUMENT ASSEMBLY

[76] Inventors: Peter J. Wilk, 185 West End Ave., New York, N.Y. 10023; David Sekons, 455 E. 86th St., New York, N.Y. 10028

[21] Appl. No.: 784,851
[22] Filed: Oct. 30, 1991
[51] Int. Cl.$^5$ ............................................. A61B 17/00
[52] U.S. Cl. ................................. 606/139; 606/144; 128/898
[58] Field of Search .................. 606/148, 139–146; 128/898

[56] References Cited

U.S. PATENT DOCUMENTS

| | | | |
|---|---|---|---|
| 4,602,635 | 7/1986 | Mulhollan et al. | 606/144 |
| 4,614,187 | 9/1986 | Mulhollan et al. | 606/144 |
| 4,621,640 | 11/1986 | Mulhollan et al. | 606/144 |
| 4,836,205 | 6/1989 | Barrett | 606/144 |
| 4,926,860 | 5/1990 | Stice et al. | 606/144 |
| 4,957,498 | 9/1990 | Caspri et al. | 606/144 |
| 5,037,433 | 8/1991 | Wilk et al. | 606/139 |

*Primary Examiner*—Stephen C. Pellegrino
*Assistant Examiner*—Gary Jackson
*Attorney, Agent, or Firm*—R. Neil Sudol; Henry D. Coleman

[57] ABSTRACT

A surgical method comprises the steps of (a) inserting a needle into a patient, a suture thread being connected to the needle, (b) moving the needle inside the patient to insert the needle into internal body tissues of the patient at a preselected surgical site inside the patient, (c) withdrawing the needle from the internal body tissues so that the suture passes through the internal body tissues, and (d) removing the needle from the patient. In a series of subsequent steps, (e) a knot is tied in the suture outside the patient, (f) the suture is manipulated to slide the knot into the patient until the knot is juxtaposed to the internal body tissues at the surgical site, (g) the suture is severed in juxtaposition to the knot at the surgical site, and (h) a severed portion of the suture is removed from the patient. A surgical instrument assembly for performing the method comprises an arcuate needle and a tubular member. The needle has a spring bias construction tending to bend the needle into an arcuate configuration and a suture thread is connected to the needle. The tubular member has an inside diameter slightly larger than an outer diameter of the needle, the needle being disposed in a straightened configuration inside the tubular member. The suture extends out through an end of the tubular member.

27 Claims, 3 Drawing Sheets

LAPAROSCOPIC SURGICAL METHOD AND RELATED INSTRUMENT ASSEMBLY

BACKGROUND OF THE INVENTION

This invention relates to a laparoscopic surgical method and a related surgical instrument assembly. More particularly, this invention relates to a surgical method and a related instrument assembly usable in a laparoscopic or endoscopic surgical procedure for performing a sewing or stitching operation on a patient's internal body tissues at a surgical site not visible to the unaided eye.

Conventional surgical techniques for repairing tissue injuries such as hernias and perforated ulcers, for closing other openings in internal body tissues and for ligating tubular body organs such as sperm ducts and Fallopian tubes, generally require that an extensive incision be made in the patient's abdominal wall. Such an operation is generally traumatic to the patient, involves considerable surgeon time and requires a relatively lengthy convalescence. This is the case even though only one or a small number of sutures is required to repair the injury or tie off the vessel.

OBJECTS OF THE INVENTION

An object of the present invention is to provide a surgical procedure for closing openings internal to a patient's body, which is less invasive than conventional surgical closure methods.

Another object of the present invention is to provide such a surgical procedure which is quicker than conventional surgical procedures and which reduces the typical postoperative convalescence period.

A related object of the present invention is to provide an improved surgical closure procedure for use in laparoscopic surgery.

Another object of the present invention is to provide an instrument assembly usable with a laparoscope for closing openings internal to a patient's body.

SUMMARY OF THE INVENTION

A surgical method in accordance with the present invention comprises the steps of (a) inserting a needle into a patient, a suture thread being connected to the needle, (b) moving the needle inside the patient so that the needle engages internal body tissues of the patient at a preselected surgical site inside the patient, (c) withdrawing the needle from the internal body tissues so that the suture passes through or around the internal body tissues, and (d) removing the needle from the patient. In a series of subsequent steps, (e) a knot is tied in the suture outside the patient, (f) the suture is manipulated to slide the knot into the patient until the knot is juxtaposed to the internal body tissues at the surgical site, (g) the suture is severed in juxtaposition to the knot at the surgical site, and (h) a severed portion of the suture is removed from the patient.

Preferably, the needle has a spring bias construction tending to bend the needle into an arcuate configuration. The method then comprises the additional step of maintaining the needle in a straightened configuration during the insertion of the needle into the patient.

The needle is maintained in a straightened configuration preferably by disposing the needle inside a narrow tubular member. In that case, the step of inserting the needle into the patient includes the step of shifting the tubular member with the needle into the patient while the needle is maintained in the straightened configuration inside the tubular member. Moving the needle inside the patient to insert the needle into internal body tissues of the patient at a preselected surgical site then comprises the step of ejecting the needle from the tubular member, whereupon the needle assumes the arcuate configuration.

In another series of preferred steps, a tube is provided and inserted into the patient. The tubular member holding the needle is then inserted into the tube and shifted therethrough to bring the needle into the patient in juxtaposition to the surgical site.

The needle is preferably withdrawn from the patient by grasping a distal tip of the needle (e.g., with a forceps inserted through the outer tube) upon passage of the needle through the internal body tissues of the patient and then pulling the needle through the tissues and through the tube until the needle is outside of the patient.

In a further step of a method in accordance with the present invention, the needle is removed from the suture prior to the tying of the suture.

A surgical instrument assembly comprises, in accordance with the present invention, an arcuate needle and a tubular member. The needle has a spring bias construction tending to bend the needle into an arcuate configuration and a suture thread is connected to the needle. The tubular member has an inside diameter slightly larger than an outer diameter of the needle, the needle being disposed in a straightened configuration inside the tubular member. The suture extends out through an end of the tubular member.

The instrument assembly may further comprise a push rod having a diameter smaller than the inside diameter of the tubular member, the push rod being inserted into the tubular member. Preferably, the needle is disposed at one end of the tubular member, the push rod having one end juxtaposed to the needle and an opposite end projecting out of the tubular member.

The instrument assembly may also comprise an additional tubular member larger in diameter than the first tubular member, the first tubular member being inserted inside the additional tubular member.

A surgical closure method in accordance with the present invention is less invasive and quicker than conventional surgical closure techniques and reduces the typical postoperative convalescence period. A surgical technique in accordance with the invention can be used in laparoscopic and endoscopic surgery to close wounds, lesions or tubular organs such as Fallopian tubes.

DETAILED DESCRIPTION

Figure 1:
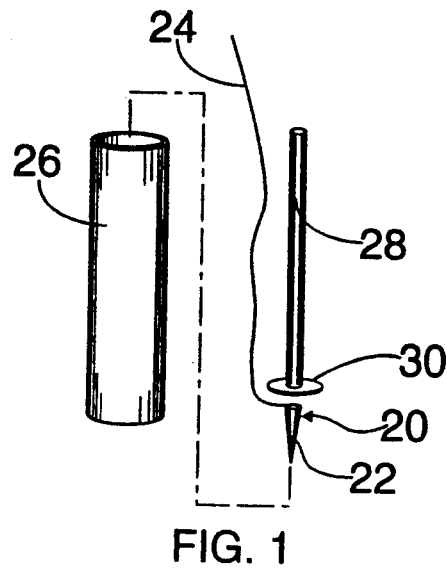
FIG. 1 is an exploded view of an instrument assembly in accordance with the present invention, for performing a surgical closure procedure for use in laparoscopic surgery, showing a suture, a needle, a push rod and a tubular needle holder.

As illustrated in FIG. 1, a surgical instrument assembly for performing a surgical closure procedure in laparoscopic surgery comprises a needle 20 having a spring bias construction tending to bend the needle into an arcuate configuration. Needle 20 has a sharp distal tip 22 and is connected at a proximal end to a suture thread 24.

Figure 2A:
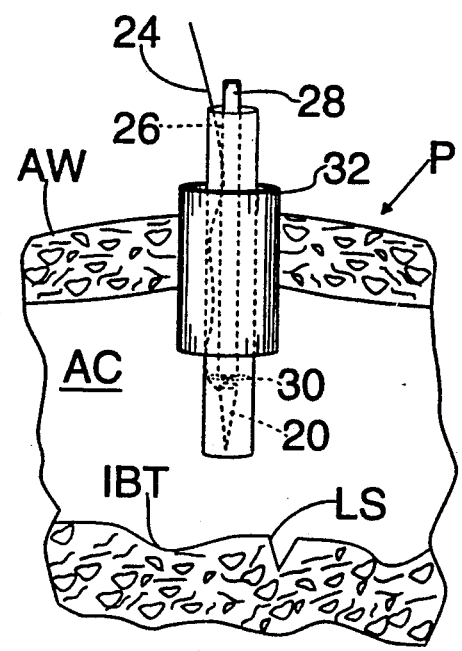
FIG. 2A is a schematic elevational view of an initial stage of a needle insertion step in a laparoscopic surgical procedure in accordance with the present invention, showing the needle of FIG. 1 inside the tubular member of FIG. 1 at a distal end thereof, and the suture and the push rod of FIG. 1 partially inside the tubular member.

Needle 20 is inserted into a tubular needle holder or insertion member 26 which has an inner diameter slightly larger than the largest diameter of needle 20, whereby needle 20 is forced to retain a straightened configuration. Generally, prior to a closure operation as shown in FIG. 2A, needle 20 is disposed at a distal end of tubular insertion member 26, while suture thread 24 extends in a proximal direction out through an opening (not labeled) at the proximal end of tubular insertion member 26. An ejector or push rod 28 is also inserted into tubular insertion member 26, the push rod projecting out from the proximal end of tubular insertion member 26. Push rod 28 is provided at a distal end with a transversely oriented planar head or flange 30 for engaging the proximal end of needle 20 during a needle ejection step, discussed in detail hereinafter with reference to FIG. 2C.

At the beginning of a laparoscopic surgical operation, the abdominal wall AW of a patient P is cut or pierced to form an opening (not labeled) through which a tubular laparoscopic member 32 is inserted to provide access to an abdominal cavity AC of the patient P. Through another opening (not shown), the distal end of a laparoscope is inserted (not shown) into cavity AC. Using the laparoscope, a surgeon is able to locate a surgical site where internal body tissues IBT evince a lesion LS or other opening requiring closure.

Figure 2B:
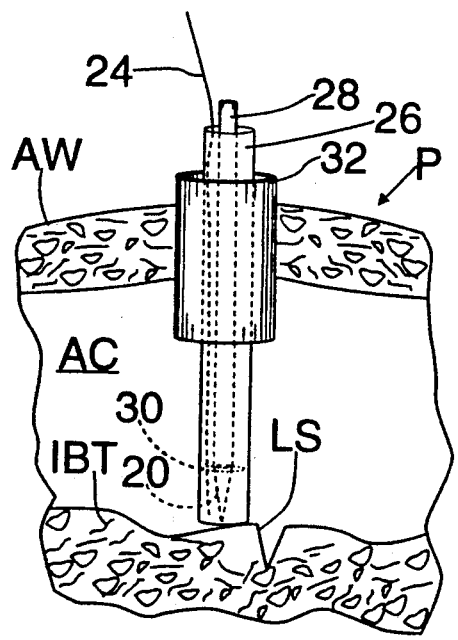
FIG. 2B is a schematic elevational view of a subsequent stage of a needle insertion step in a laparoscopic surgical procedure in accordance with the present invention.
Figure 2C:
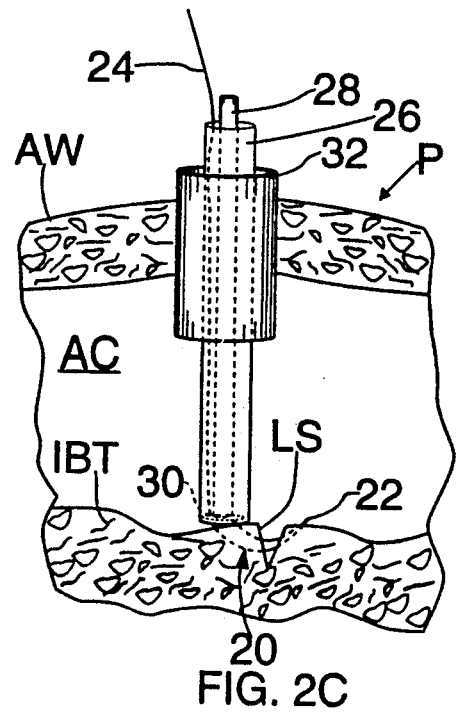
FIG. 2C is a schematic elevational view showing a needle ejection step in a laparoscopic surgical procedure in accordance with the present invention.

Using the laparoscope to visually monitor the surgical site, the surgeon inserts tubular insertion member 26 with needle 20 and push rod 28 through tubular laparoscopic member 32 into the patient's abdominal cavity AC, as shown in FIG. 2A. Upon juxtaposition of the distal end of tubular insertion member 26, and hence needle 20, with internal body tissues IBT, as illustrated in FIG. 2B, push rod 28 is shifted in the distal direction to eject needle 20 from tubular insertion member 26 and into the body tissues IBT of the patient proximately to lesion or wound LS. Because of the internal spring bias of needle 20, the needle bends during its passage through tissues IBT. Accordingly, at the end of a needle ejection operation, implemented via push rod 28, the distal tip 22 of needle 20 protrudes slightly from the internal body tissues (FIG. 2C).

Figure 2D:
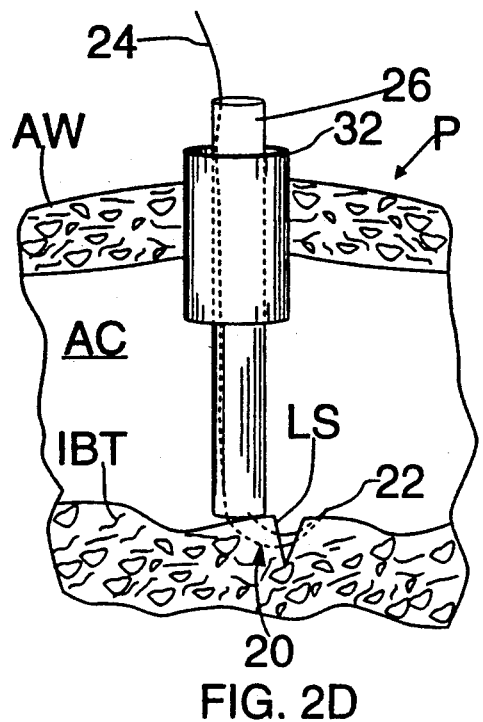
FIG. 2D is a schematic elevational view of the tubular needle holder of FIG. 1 with the push rod of that figure removed in a later stage of a laparoscopic surgical procedure in accordance with the present invention.
Figure 2E:
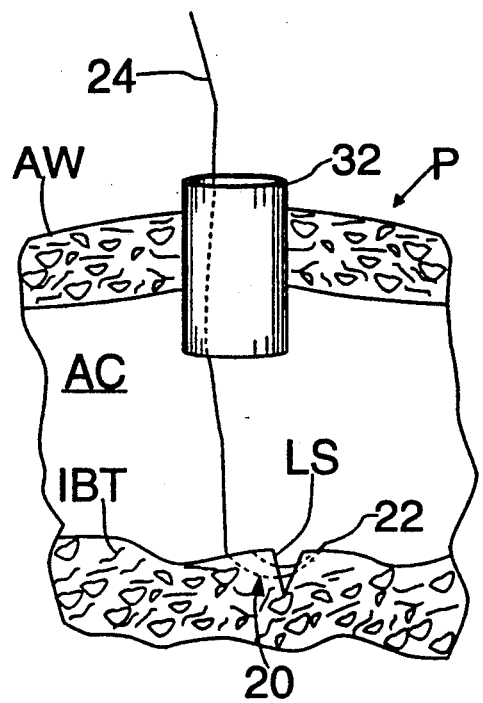
FIG. 2E is a schematic elevational view showing the tubular needle holder removed in a laparoscopic surgical procedure in accordance with the present invention.
Figure 2F:
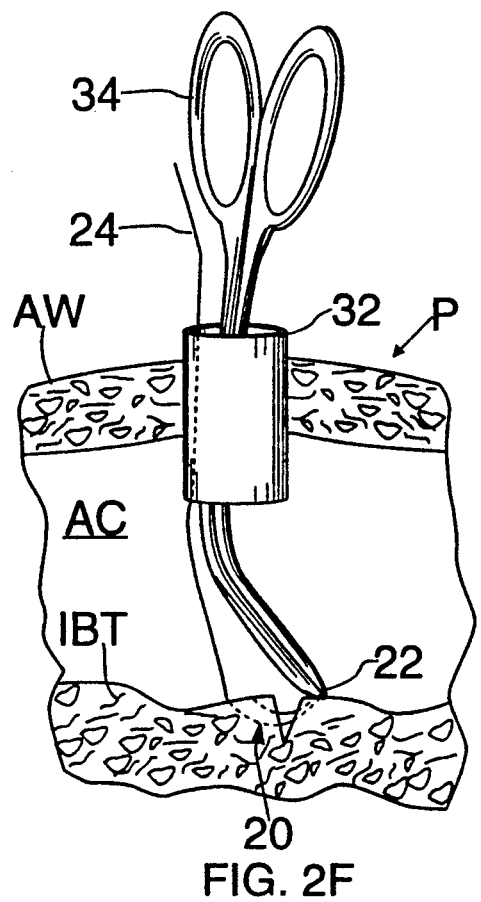
FIG. 2F is a schematic elevational view depicting a grasping forceps inserted into a patient's body in a laparoscopic surgical procedure in accordance with the present invention.
Figure 2G:
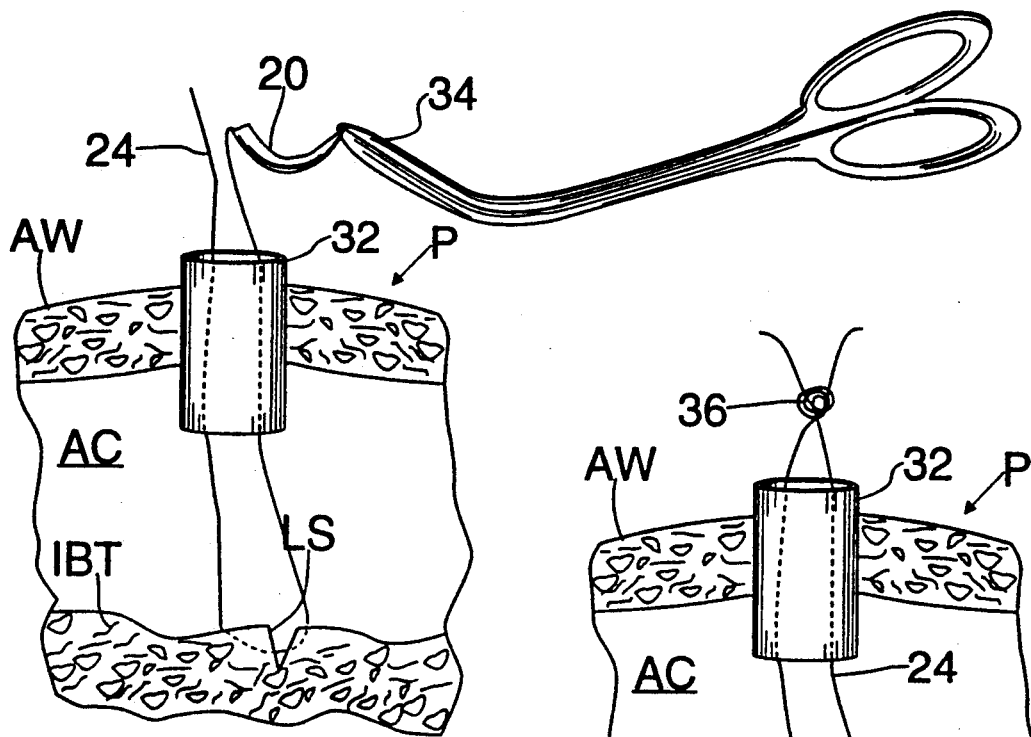
FIG. 2G is a schematic elevational view of the grasping forceps and the surgical needle of FIG. 2F removed from the patient's body in a subsequent step of a laparoscopic surgical procedure in accordance with the present invention.

At this juncture, push rod 28 is removed from tubular insertion member 26, as indicated in FIG. 2D. Subsequently, as depicted in FIG. 2E, tubular insertion member 26 is withdrawn from the surgical site and through tubular laparoscopic member 32. A grasping forceps 34 is now inserted through tubular laparoscopic member 32 into abdominal cavity AC and is manipulated to grasp the protruding tip 22 of needle 20, as shown in FIG. 2F. Forceps 34, together with needle 20, is then withdrawn from abdominal cavity AC through tubular laparoscopic member 32, as shown in FIG. 2G.

Figure 2H:
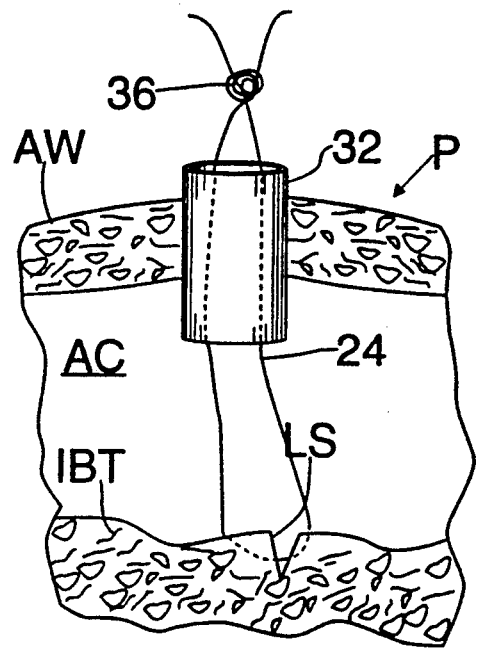
FIG. 2H is a schematic elevational view representing the tying of the suture of FIG. 1 to form a knot outside of the patient's body in a laparoscopic surgical procedure in accordance with the present invention.
Figure 2I:
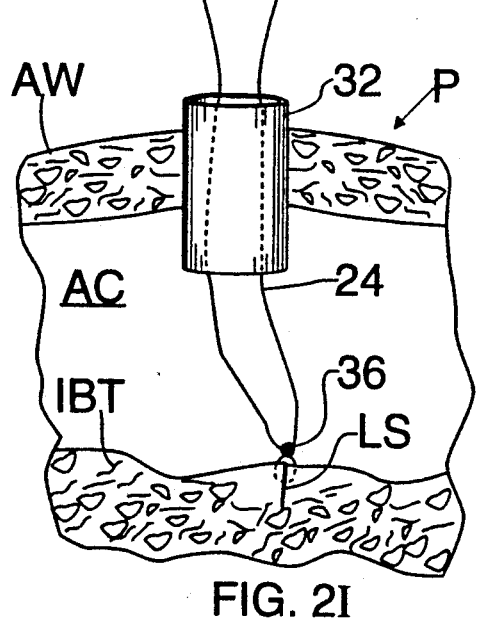
FIG. 2I is a schematic elevational view showing the knot of FIG. 2H slid down to a surgical site in a laparoscopic surgical procedure in accordance with the present invention.
Figure 2J:
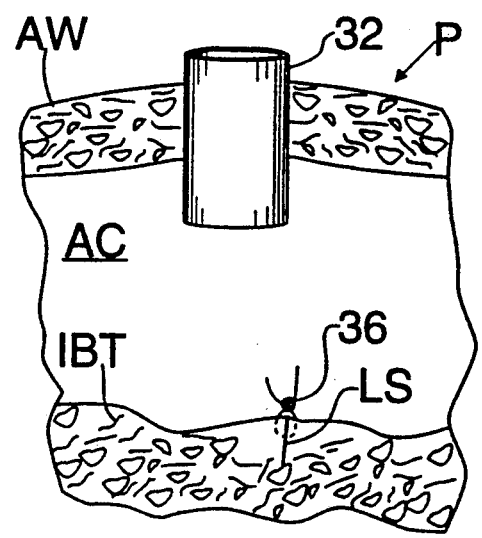
FIG. 2J is a schematic elevational view showing tail ends of the suture removed from the knot in a laparoscopic surgical procedure in accordance with the present invention.

Upon the removal of needle 20 from abdominal cavity AC via tubular laparoscopic member 32, the needle 20 is separated from suture 24. The ends of suture thread 24 are then tied, as indicated in FIG. 2H, to form a slip knot 36. Suture thread 24 is manipulated to slide knot 36 down through tubular laparoscopic member 32 and into abdominal cavity AC so that the knot is juxtaposed to or engages the patient's internal body tissues IBT at the lesion LS, whereupon the lesion is at least partially closed (see FIG. 2I). A cutting instrument (not shown) is then inserted through tubular laparoscopic member 32 and manipulated so that suture thread 24 is severed in the region of knot 36. The severed portion(s) of the suture thread 24 are then drawn out of the patient, as shown in FIG. 2J.

Although the invention has been described in terms of particular embodiments and applications, one of ordinary skill in the art, in light of this teaching, can generate additional embodiments and modifications without departing from the spirit of or exceeding the scope of the claimed invention. For example, it will be clear to one skilled in the surgical arts that the techniques of the instant invention may be used to close tubular organs such as Fallopian tubes and will have applications in selected endoscopic procedures, as well. Accordingly, it is to be understood that the drawings and descriptions herein are preferred by way of example to facilitate comprehension of the invention and should not be construed to limit the scope thereof.

What is claimed is:

1. A surgical method comprising the steps of:
   providing a needle having a spring bias construction tending to bend said needle into an arcuate configuration, said needle having a sharp distal tip, a suture thread being connected to said needle;
   introducing said needle into a patient through a tubular member, while exerting a force on said needle to maintain said needle in a straightened configuration;

juxtaposing said needle to internal body tissues of the patient at a preselected surgical site;

upon juxtaposition of said needle and said internal body tissues, pushing said needle into engagement with said internal body tissues of said patient at said surgical site, while releasing said force, thereby permitting said needle to assume said arcuate configuration;

grasping said distal tip of said needle upon engagement of said needle with said internal body tissues;

pulling said needle through or around said internal body tissues and through said tubular member until said needle is outside of the patient;

tying a knot in said suture outside the patient;

manipulating said suture to slide said knot through said tubular member into the patient until said knot is juxtaposed to said internal body tissues at said surgical site;

severing said suture at said knot;

and removing a severed portion of said suture from the patient through said tubular member.

2. The method defined in claim 1, further comprising the step of providing an additional tubular member having a smaller diameter than the first tubular member, said suture being disposed in said straightened configuration inside said additional tubular member, said step of introducing comprising the step of inserting said additional tubular member into said first tubular member.

3. The method defined in claim 2, further comprising the step of providing a push rod having a distal end juxtaposable to said needle inside said additional tubular member, said step of pushing comprising the step of ejecting said needle from said additional tubular member by manipulation of said push rod.

4. The method defined in claim 1 wherein said step of grasping comprises the steps of inserting a forceps member into the patient through said tubular member and manipulating said forceps to engage said distal tip of said needle, said step of pulling comprising the step of pulling said forceps member out through said tubular member.

5. The method defined in claim 1, further comprising the step of tightening said knot at said internal body tissues prior to said step of severing.

6. The method defined in claim 1, further comprising the step of removing said needle from said suture prior to said step of tying.

7. A surgical method comprising the steps of:
inserting a needle into a patient, a suture thread being connected to said needle, said needle having a spring bias construction tending to bend said needle into an arcuate configuration;
maintaining said needle in a straightened configuration during said step of inserting;
moving said needle inside said patient so that said needle engages internal body tissues of the patient at a preselected surgical site inside the patient;
withdrawing said needle from said internal body tissues so that said suture passes through or around said internal body tissues;
removing said needle from the patient;
tying a knot in said suture outside the patient;
manipulating said suture to slide said knot into the patient until said knot is juxtaposed to said internal body tissues at said surgical site;
severing said suture in juxtaposition to said knot at said surgical site; and
removing a severed portion of said suture from the patient.

8. The method defined in claim 7 wherein said step of maintaining includes the step of keeping said needle disposed inside a narrow tubular member, said step of inserting including the step of shifting into the patient said tubular member with said needle in said straightened configuration, said step of moving including the step of ejecting said needle from said tubular member, whereupon said needle assumes said arcuate configuration.

9. The method defined in claim 8, further comprising the steps of providing a tube and inserting said tube into the patient, said step of shifting comprising the step of inserting said tubular member into said tube, said step of inserting including the step of moving said tubular member with said needle through said tube.

10. The method defined in claim 7, further comprising the steps of providing a tube and inserting said tube into the patient, said steps of inserting and removing each including the step of moving said needle through said tube.

11. The method defined in claim 10 wherein said step of withdrawing includes the steps of:
grasping a distal tip of said needle upon passage thereof through said internal body tissues; and
pulling said needle through said tissues and through said tube until said needle is outside of the patient.

12. The method defined in claim 7, further comprising the step of removing said needle from said suture prior to said step of tying.

13. A surgical method comprising the steps of:
inserting a needle into a patient, said needle having a spring bias construction tending to bend said needle into an arcuate configuration, a suture thread being connected to said needle;
maintaining said needle in a straightened configuration during said step of inserting;
moving said needle inside said patient so that said needle partially surrounds an internal organic structure of the patient at a preselected surgical site inside the patient;
withdrawing said needle from the patient so that said suture passes around said internal organic structure;
tying a knot in said suture outside the patient;
manipulating said suture to slide said knot into the patient until said knot is juxtaposed to said internal organic structure at said surgical site;
severing said suture in juxtaposition to said knot at said surgical site; and
removing a severed portion of said suture from the patient.

14. A surgical instrument assembly comprising:
an arcuate needle having a spring bias construction tending to bend said needle into an arcuate configuration, a suture thread being connected to said needle; and
a tubular member having an inside diameter slightly larger than an outer diameter of said needle, said needle being disposed in a straightened configuration inside said tubular member, said suture extending out through an end of said tubular member.

15. The instrument assembly defined in claim 14, further comprising a push rod having a diameter smaller than said inside diameter, said push rod being inserted into said tubular member.

16. The instrument assembly defined in claim 15 wherein said needle is disposed at one end of said tubular member, said push rod having one end juxtaposed to said needle and an opposite end projecting out of said tubular member.

17. The instrument assembly defined in claim 15, further comprising an additional tubular member larger in diameter than the first tubular member, said first tubular member being inserted inside said additional tubular member.

18. A surgical method comprising the steps of:
disposing a first tubular member in a skin surface of a patient so that said first tubular member traverses said skin surface;
providing a needle having a sharp distal tip, a suture thread being connected to said needle;
disposing said needle inside a second tubular member;
introducing a portion of said second tubular member with said needle into a body cavity of the patient through said first tubular member;
juxtaposing a distal end of said second tubular member to internal body tissues of the patient at a preselected surgical site in said body cavity;
upon juxtaposition of said distal end of said second tubular member and said internal body tissues, pushing said needle out of said second tubular member through said internal body tissues of said patient at said surgical site;
inserting a grasping instrument into said body cavity; and
operating said grasping instrument from outside the patient to grasp said needle, upon pushing of said needle at least partially through said internal body tissues, and to manipulate said needle to facilitate formation of a closure with said suture.

19. The method defined in claim 18 wherein said step of inserting includes the step of inserting said grasping instrument through said first tubular member, said step of operating including the step of pulling said needle through said first tubular member until said needle is outside of the patient, further comprising the steps of:
tying a knot in said suture outside the patient;
manipulating said suture to slide said knot through said first tubular member into the patient until said knot is juxtaposed to said internal body tissues at said surgical site;
severing said suture at said knot; and
removing a severed portion of said suture from the patient through said first tubular member.

20. The method defined in claim 19, further comprising the step of tightening said knot at said internal body tissues prior to said step of severing.

21. The method defined in claim 19, further comprising the step of removing said needle from said suture prior to said step of tying.

22. The method defined in claim 18 wherein said needle has a spring bias construction tending to bend said needle into an arcuate configuration, further comprising the step of exerting a force on said needle via said second tubular member to maintain said needle in a straightened configuration during said step of introducing, also comprising the step of releasing said force upon pushing of said needle from said second tubular member, thereby permitting said needle to assume said arcuate configuration.

23. The method defined in claim 18, further comprising the step of providing a push rod having a distal end juxtaposable to said needle inside said second tubular member, said step of pushing comprising the step of ejecting said needle from said additional tubular member by manipulation of said push rod.

24. A surgical method comprising the steps of:
disposing a first tubular member in a skin surface of a patient so that said first tubular member traverses said skin surface;
providing an elongate suturing member, a suture thread being connected to said suturing member;
disposing said suturing member inside a second tubular member;
introducing a portion of said second tubular member with said suturing member into a body cavity of the patient through said first tubular member;
ejecting said suturing member out from a distal end of said second tubular member;
inserting a grasping instrument into said body cavity;
manipulating said grasping instrument to move said suturing member inside the body cavity of the patient so that said suturing member partially surrounds an internal organic structure of the patient at a preselected surgical site inside the patient; and
closing said suture about said organic structure.

25. The method defined in claim 24 wherein said step of closing includes the steps of:
operating said grasping instrument to pull said suturing member through said first tubular member until said suturing member is outside of the patient;
tying a knot in said suture outside the patient;
manipulating said suture to slide said knot through said first tubular member into the patient until said knot is juxtaposed to said internal organic structure;
severing said suture at said knot; and
removing a severed portion of said suture from the patient through said first tubular member.

26. The method defined in claim 24 wherein said suturing member has a spring bias construction tending to bend said suturing member into a arcuate configuration, further comprising the step of exerting a force on said suturing member via said second tubular member to maintain said suturing member in a straightened configuration during said step of introducing, also comprising the step of releasing said force upon pushing of said suturing member from said second tubular member, thereby permitting said suturing member to assume said arcuate configuration.

27. The method defined in claim 24 wherein said suturing member is a needle.

* * * * *